United States Patent
Hart et al.

(10) Patent No.: US 10,228,323 B1
(45) Date of Patent: Mar. 12, 2019

(54) SYSTEMS AND METHODS FOR OPTICALLY DETERMINING AN ACOUSTIC SIGNATURE OF AN OBJECT

(71) Applicants: Michael Hart, Tucson, AZ (US); Zachary Watson, Tucson, AZ (US)

(72) Inventors: Michael Hart, Tucson, AZ (US); Zachary Watson, Tucson, AZ (US)

(*) Notice: Subject to any disclaimer, the term of this patent is extended or adjusted under 35 U.S.C. 154(b) by 0 days.

(21) Appl. No.: 15/921,501

(22) Filed: Mar. 14, 2018

Related U.S. Application Data (60) Provisional application No. 62/470,979, filed on Mar. 14, 2017.

(51) Int. Cl.
| | |
|---|---|
| *G01N 21/21* | (2006.01) |
| *G02B 27/28* | (2006.01) |
| *G01N 21/17* | (2006.01) |
| *G02B 23/04* | (2006.01) |

(52) U.S. Cl.
CPC ......... *G01N 21/21* (2013.01); *G01N 21/1702* (2013.01); *G02B 23/04* (2013.01); *G02B 27/283* (2013.01); *G01N 2201/0638* (2013.01); *G01N 2201/0683* (2013.01)

(58) Field of Classification Search
CPC .... G01N 21/21; G01N 21/1702; G02B 23/04; G02B 27/283
USPC ......................................................... 356/369
See application file for complete search history.

(56) References Cited

U.S. PATENT DOCUMENTS

| | | | |
|---|---|---|---|
| 6,677,571 B1 | 1/2004 | Clark et al. ................ 250/214.1 |
| 6,731,570 B1 * | 5/2004 | Langdon ................ G01H 9/002 |
| | | | 356/450 |
| 8,284,405 B1 | 10/2012 | Clark ........................... 356/447 |
| 8,659,686 B1 | 2/2014 | Clark ........................... 348/270 |
| 8,927,915 B1 | 1/2015 | Clark ........................... 244/3.16 |
| 10,037,609 B2 | 7/2018 | Chen et al. ............. G06T 7/246 |
| 2008/0151694 A1 | 6/2008 | Slater ............................ 367/178 |
| 2014/0132761 A1 | 5/2014 | Shih et al. ........... G01B 11/303 |
| 2015/0319540 A1 | 11/2015 | Rubinstein et al. .. H04R 23/008 |
| 2016/0113507 A1 * | 4/2016 | Reza .................. G01N 21/1717 |
| | | | 356/477 |
| 2016/0267664 A1 | 9/2016 | Davis et al. .......... G06T 7/0046 |

(Continued)

OTHER PUBLICATIONS

Clarke, D., "Theoretical Considerations in the Design of an Astronomical Polarimeter," MRNAS, vol. 129, p. 71-84, 1964 (14 pgs).

(Continued)

*Primary Examiner* — Roy M Punnoose
(74) *Attorney, Agent, or Firm* — Hayes Soloway P.C.

(57) ABSTRACT

A photo-acoustic polarimetric remote sensing apparatus includes a telescope that directs visible light photons from an object. A polarizing beam splitter is in optical alignment with the telescope. The polarizing beam splitter has first and second pathways corresponding to first and second polarization states, respectively. The first and second pathways are substantially perpendicular. A first photodetector is in optical alignment with the first pathway, and a second photodetector is in optical alignment with the second pathway. At least one processor is in communication with the first and second photodetectors. The at least one processor generates a signal corresponding to a degree of linear polarization of the photons over time, and the signal is indicative of an acoustic signature of the object.

20 Claims, 6 Drawing Sheets

(56) References Cited

U.S. PATENT DOCUMENTS

2017/0215738 A1\* 8/2017 Hajireza .............. A61B 5/0095
2018/0061063 A1 3/2018 Buyukozturk et al. ... G06T 7/20

OTHER PUBLICATIONS

Jorgensen et al., Reflectance Spectra of Human-made Objects, 2004 AMOS Technical Conference, Wailea, Maui, Hawaii, Sep. 8-12, 2004 (12 pgs).
Schott, J.R., "Fundamentals of Polarimetric Remote Sensing," SPIE Press, Bellingham Washington. 2009 (263 pgs).
Slater et al., "Photo-acoustic and video-acoustic methods for sensing distant sound sources," Long-Range Imaging II (Proc. SPIE), 10204, 1020408, 2017 (10 pgs).
de Selding, P. Space Intel Report. Jul. 2, 2017. SES re-establishes communications with AMC-9; pieces of satellite appear to have broken off. Online at: https://www.spaceintelreportcom/ses-se-establishes-communications-amc-9-pieces-satellite-appear-broken-off/ (5 pgs).
Watson et al., "Remote Acoustic Imaging of Geosynchronous Satellites," 2017 AMOS Technical Conference, Wailea, Maui, Hawaii, Sep. 19-22, 2017 (8 pgs).

\* cited by examiner

SYSTEMS AND METHODS FOR OPTICALLY DETERMINING AN ACOUSTIC SIGNATURE OF AN OBJECT

CROSS REFERENCE TO RELATED APPLICATION

This application claims benefit of U.S. Provisional Application No. 62/470,979, entitled, "Systems and Methods for Optically Determining an Acoustic Signature of an Object" filed Mar. 14, 2017, the entire disclosure of which is incorporated herein by reference.

FIELD OF THE DISCLOSURE

The present disclosure is generally related to remote sensing using light, and in particular is directed to remote sensing using polarization of light to determine an acoustic signature of a remote object.

BACKGROUND OF THE DISCLOSURE

In the modern age of space technology, reliance on satellites is significant and growing. The United Nations estimates that there are currently more than 4,000 satellites orbiting the Earth, with more than 1,000 predicted to launch over the next several years. These satellite devices have a broad span of technical uses, ranging from commercial, to civil, to military applications. Thousands of additional space debris objects are in orbit as well.

Objects in geosynchronous Earth orbits (GEO) are located about 36,000 kilometers away from Earth. At that distance, they represent a special challenge to monitor using imaging methods. Traditional means, using Earth-based remote sensing, have generally been ineffective, even with large-scale apertures and expensive equipment. However, identification and monitoring of GEO objects remains an important issue. Satellites have limited life-spans given the harsh environment of space, where weathering degrades craft thermal surfaces, and the wearing of mechanical features can lead to critical component failure. Improved characterization and prediction may lead to mitigation strategies in the event of imminent on-orbit failure. Furthermore, satellite identification and cross-tagging, as well as the recognition of changes in the behavior of a satellite, whether driven by phenomena internal or external to the satellite itself, is important in defending against military and national security threats.

Thus, a heretofore unaddressed need exists in the industry to address the aforementioned deficiencies and inadequacies.

SUMMARY OF THE DISCLOSURE

Embodiments of the present disclosure provide a system and apparatus for remotely sensing an object using photo-acoustic polarization characteristics. Briefly described, in architecture, one embodiment of the apparatus, among others, can be implemented as follows. A photo-acoustic polarimetric remote sensing apparatus includes a telescope that directs visible light photons from an object. A polarizing beam splitter is in optical alignment with the telescope. The polarizing beam splitter has first and second pathways corresponding to first and second polarization states, respectively. The first and second pathways are substantially perpendicular. A first photodetector is in optical alignment with the first pathway, and a second photodetector is in optical alignment with the second pathway. At least one processor is in communication with the first and second photodetectors. The at least one processor generates a signal corresponding to a degree of linear polarization of the photons over time, and the signal is indicative of an acoustic signature of the object.

The present disclosure also provides an apparatus for remotely sensing an object using photo-acoustic polarization characteristics. Briefly described, in architecture, one embodiment of the apparatus can be implemented as follows. A photo-acoustic polarimetric remote sensing apparatus includes collection optics that direct photons. A polarizing beam splitter has first and second pathways, where photons within the first and second pathways have first and second polarization states, respectively. A first optical detector is located in the first pathway, and a second optical detector is located in the second pathway. At least one processor is in communication with the first and second optical detectors. The at least one processor: receives first and second signals from the first and second optical detectors, respectively; calculates, for a segment of the first and second signals, a difference of the first and second signals, a sum of the first and second signals, and a ratio of the difference to the sum; and generates, for a plurality of segments a signal corresponding to a sequential output of the ratio for each segment. The signal is indicative of an acoustic signature of an object being sensed.

The present disclosure can also be viewed as providing methods of remotely sensing an object using photo-acoustic polarization characteristics. In this regard, one embodiment of such a method, among others, can be broadly summarized by the following steps: collecting photons from the object; directing the photons down first and second pathways, wherein photons within the first pathway have a first polarization state and photons within the second pathway have a second polarization state; detecting photons in the first and second pathways using at least one optical detector, wherein the photons in the first polarization state produce a first signal and the photons in the second polarization state produce a second signal; receiving, with at least one processor in communication with the first and second optical detectors, a first signal and a second signal; determining, with the at least one processor and for a segment of the first and second signals, a difference of the first and second signals, a sum of the first and second signals, and a ratio of the difference to the sum; and generating, for a plurality of segments, a signal corresponding to a sequential output of the ratio for each segment.

The present disclosure can also be viewed as providing a system and apparatus for remotely sensing an object using photo-acoustic polarization characteristics. Briefly described, in architecture, one embodiment of the apparatus can be implemented as follows. A photo-acoustic polarimetric remote sensing apparatus includes collection optics that direct photons. A polarizing prism angularly separates the photons into a first polarization state and a second polarization state. An optical detector is included. A first portion of the optical detector receives the photons in the first polarization state, and a second portion of the optical detector receives the photons in the second polarization state. At least one processor is in communication with the optical detector. The at least one processor: receives a signal from the optical detector, wherein a first portion of the signal corresponds to the photons in the first polarization state, and a second portion of the signal corresponds to the photons in the second polarization state; calculates, for a segment of the first and second signals, a difference of the first and second portions of the signals, a sum of the first and second portions of the signals, and a ratio of the difference to the sum; and generates, for a plurality of segments, a signal corresponding to a sequential output of the ratio for each segment. The signal is indicative of an acoustic signature of an object being sensed.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

DETAILED DESCRIPTION

Aspects of the invention will be further illustrated with reference to the following specific examples. It is understood that these examples are given by way of illustration and are not meant to limit the disclosure or the claims to follow.

Figure 1:
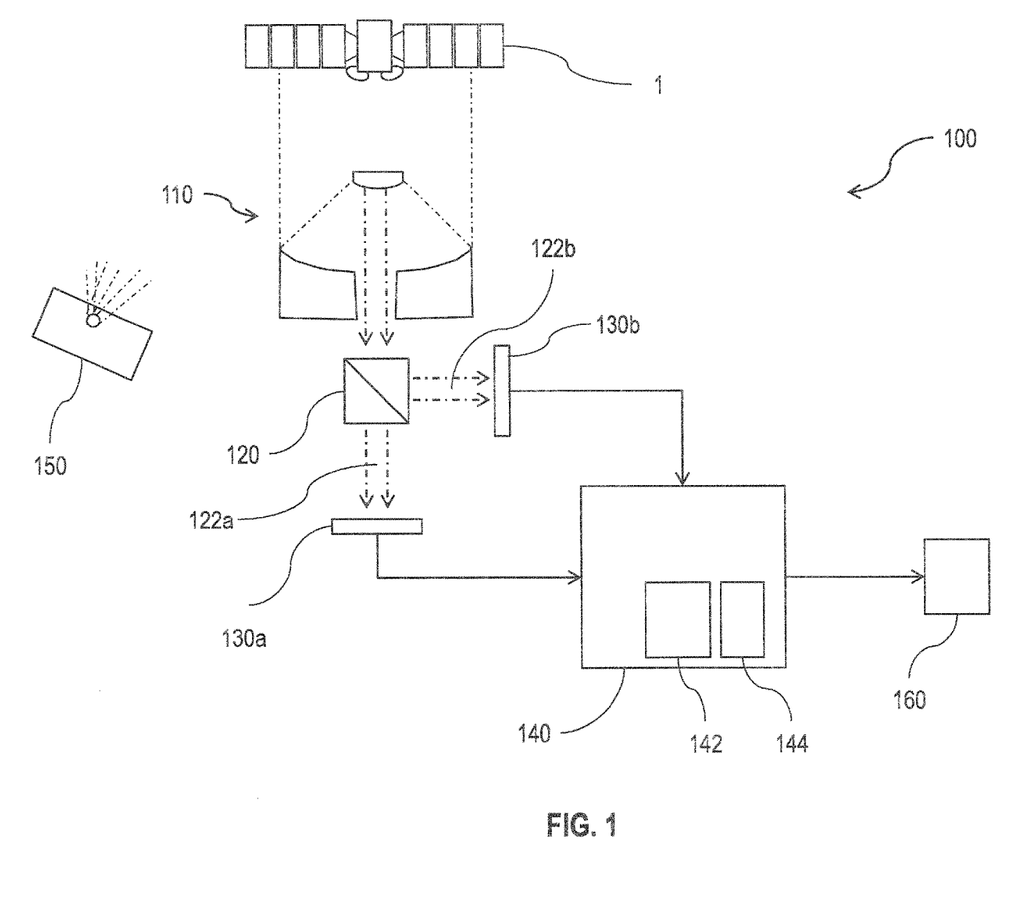
FIG. 1 is a schematic block diagram of an example of a remote sensing apparatus, in accordance with a first exemplary embodiment of the present invention.

FIG. 1 is a schematic block diagram of a remote sensing apparatus 100 in accordance with a first exemplary aspect of the present invention. The apparatus 100 includes collection optics 110 directing photons from an object 1. A polarizing beam splitter 120 has first and second pathways 122a, 122b. Photons within the first and second pathways 122a, 122b have first and second polarization states, respectively. The apparatus 100 also includes a first optical detector 130a located in the first pathway 122a and a second optical detector 130b located in the second pathway 122b. At least one processor 140 is in communication with the first and second optical detectors 130a, 130b. The at least one processor 140 is configured to: receive first and second signals from the first and second optical detectors 130a, 130b, respectively; calculate, for a segment of the first and second signals, a difference of the first and second signals, a sum of the first and second signals, and a ratio of the difference to the sum; and generate, for a plurality of segments, a signal corresponding to the sequential output of the ratio for each segment, wherein the signal is indicative of an acoustic signature of the object 1 being sensed.

The object 1 may be any remote object. For example, the object 1 may be an object 1 in space, such as a satellite, spacecraft, space station, and the like, in geosynchronous orbit. The object 1 may be an object 1 within the Earth's atmosphere, such as an airplane, weather balloon, missile, and the like. The object 1 may be a remote object 1 on Earth, commonly referred to as a terrestrial object, such as a structure, building, vehicle, and the like. Multiple objects 1 may also be viewed simultaneously or in succession, for instance, several satellites or a combination of space objects and other objects. In one example when viewing multiple objects 1, the apparatus 100 may focus on the objects 1 individually, one at a time. In another example, the apparatus 100 may detect all objects 1 within its field of view and may separate or resolve each object 1 during analysis. In another example, the apparatus 100 may focus on an atmospheric layer using conjugate planes, instead of focusing on the object 1. Focusing on an atmospheric layer may improve the overall signal-to-noise ratio by reducing noise introduced by scintillation.

The photons may be from any suitable band of the electromagnetic spectrum, for example, the infrared, visible, ultraviolet, or x-ray bands. In use, the suitable band may be different depending on the object 1 being sensed. For instance, if a portion or entirety of the object 1 is optically transparent to some bands, but optically reflective to others, the reflective bands may be more useful in detection. As another example, if an object 1 is located in an area where there is no incident light from a portion of the spectrum, it may not be useful to detect photons from that portion of the spectrum. In one example, the apparatus 100 may include additional optical detectors or optical detectors 130a, 130b capable of detecting photons in multiple bands. Results from each band may be used to provide increased contrast, resolution, or detail in the final results. Depending on the implementation of the collection optics 110 and sensors 130a, 130b, the apparatus 100 may receive a broad or narrow band of photons.

Collection optics 110 operate to collect photons from object 1 in sufficient quantity to achieve a desired signal-to-noise performance. The collection optics 110 may be any collectors suitable to collect light from the desired band. For example, collection optics 110 may constitute any known or yet to be developed telescope design, including reflective and/or refractive optical elements. As shown in FIG. 1, and by way of example, the collection optics 110 may be configured as a Cassegrain telescope. As another example, Gregorian, modified Dahl-Kirkham, Keplerian, or Ritchey-Chretien telescopes may be used. The collection optics 110 may include one or more steering optics to direct the photons to the beam splitter 120. The apparatus 100 may additionally include other common optical elements, such as collimators, filters, prisms, beam sizers, and the like.

Polarizing beam splitter 120 may be any suitable polarizing beam splitter for use with the intended spectral band. This may include cube beam splitters, plate beam splitters, high energy beam splitters, wire grid beam splitters, lateral displacement beam splitters, and the like. In one example, the polarizing beam splitter 120 may be a 50/50 cube beam splitter positioned to split outgoing light by a lateral angle of 90°. Light transmitted through the beam splitter 120 travels along a first pathway 122a to first optical detector 130a. Light that reflects off the beam splitter 120 travels along a second pathway 122b to a second optical detector 130b. The optical detectors 130a, 130b may be aligned with the pathways 122a, 122b such that incident light strikes the optical detectors 130a, 130b normal to the surface of the optical detectors 130a, 130b. Light traveling along the first pathway 122a may have a first polarization state, while light traveling along the second pathway may have a second polarization state. For example, transmitted light may be P-polarized and reflected light may be S-polarized.

Separating the photons into two polarized portions provides two benefits. First, as described in greater detail below, the presence of two portions allows the apparatus 100, through processing, to achieve common mode rejection for signals subject to atmospheric scintillation or other noise-inducing phenomena. This is most common for non-terrestrial objects, such as satellites and spacecraft. An incident beam that has not been split will indicate the total intensity when read by an optical detector 130a, 130b. However, the total intensity is subject to scintillation, the variation in the apparent brightness or position of the object 1, that may mask or be mistaken for the acoustic signature. Therefore, rather than relying on total intensity, the apparatus 100 synchronously measures the intensities in the two orthogonal polarization states separately. In this way, variations due to apparent brightness or position of the object 1 can be compared across the first and second polarization states. Variations common to both states may indicate scintillation, and may be discarded or otherwise not considered. Additionally, measurements using total intensity may be highly sensitive to local vibrations in the sensing apparatus. The common mode rejection achieved by separating the beams may overcome this issue by allowing the apparatus 100 to discard variations induced by vibration that are common to both states.

Second, the presence of two signals with different polarization states allows the apparatus 100 to identify differences between the two signals, as well as changes in the differences between the signals, to determine characteristics of object 1, or a portion of object 1, over time, as described in greater detail below. It will be appreciated that changes in the differences over time may vary, for example, in response to vibrations of the object 1, causing a ratio of the quantities of light in the pathways to vary. The ratio is indicative of an acoustic signature of the object 1. Such variations may be particularly present where the collected photons are reflected from a man-made object. Man-made objects tend to have flat or partially flat surface structures made of certain materials, such that the polarization content of the light specularly reflected from the object is indicative of the nature of the object. For example, metallic surfaces may reflect polarized light differently relative to the polarization state of the light. Light in a first polarization state may be strongly reflected at certain times, angles, or under other conditions. Light in a second polarization state may be strongly reflected under different times, angles, or other conditions. Non-metallic surfaces may behave in a similar way. For example, solar panels, which are common to most satellites and spacecraft, present flat surfaces that may reflect polarized light differently. It may be expected that any acoustic oscillations from the solar panels will induce change in both the angle and degree of polarized light reflected.

The construction of beam splitter 120 is selected so that the beam splitter operates in the selected band of the electromagnetic spectrum. For example, a polarizing beam splitter may be glass, calcite or be of a wire grid construction, although any other suitable beam splitter may be used.

As described above, polarizing beam splitter 120 may separate the light into two pathways 122a, 122b, where the light in the first pathway 122a is linearly polarized in a first direction and the light in the second pathway 122b is linearly polarized in a second direction that is orthogonal to the first direction. In one example the light in each pathway 122a, 122b is linearly polarized, the light being P and S-polarized, respectively. In another example, the light may be separated according to polarization such that first pathway is polarized to have light of a first Stokes parameter and the second pathway is polarized to have light of a second Stokes parameter. For instance, the first pathway 122a may be linearly polarized with its electric field aligned vertically, and the second pathway 122b may be linearly polarized with its electric field aligned horizontally. Alternatively, the first pathway 122a may be linear polarized with its electric field aligned at 45 degrees to vertical, and the second pathway 122b may be linearly polarized with its electric field at 45 degrees to vertical and orthogonal to the first pathway 122a. In another example, the first pathway 122a may be circularly polarized in a first direction and the second pathway 122b may be circularly polarized in a direction opposite to the first direction.

In one example, the propagation of the first pathway-122a may be substantially perpendicular to the direction of propagation of the second pathway 122b. For example, many polarizing cube beam splitters direct the reflected beam at about a 90° angle relative to the transmitted beam. Plate beam splitters and other reflective polarizers may be positioned at an appropriate angle, usually about 45°, to achieve a 900 beam separation as well.

First optical detector 130a is located in the first pathway 122a and receives photons in the first polarization state. Second optical detector 130b is located in the second pathway 122b and receives photons in the second polarization state. In one example, the optical detectors 130a, 130b may be optically aligned to receive the photons at a normal incident angle and at an optimal focal point. In another example, first and/or second pathways 122a, 122b may also include filter wheels, focal elements such as lenses, and other optical components. The optical detectors 130a, 130b may each produce a signal indicative of the quantity of photons received.

In one example, the collection optics 110 produce an image of the object 1 on the first and the second optical detectors 130a, 130b. The optical detectors 130a, 130b may be pixelated to receive spatial information about pathways of the image incident thereon. Pixelated detectors may indicate the location of the source of polarized photons relative to the object 1 as a whole. For example, pixelated detectors may indicate that a particular acoustic frequency is emanating from the top of an object 1, which may assist in identification or verification of operation. The optical detectors 130a, 130b may be any detectors suitable to operate in the selected band or bands of the electromagnetic spectrum, including CCD and CMOS devices. For instance, the optical detectors 130a, 130b may be a camera, such as a FLIR Flea® 3 CCD camera or FLIR Grasshopper® 3 CMOS camera. In another example, the detectors 130a, 130b may be other photodetectors, such as photodiodes, amplified detectors, integrating spheres, biased detectors, and the like. In yet another example, the detectors 130a, 130b may be different types of detectors, depending on implementation. In another example, the detectors 130a, 130b may be identical.

In some examples, collection optics 110 collect photons from the object 1 without forming an image. In those cases where an image is not generated or where image information is not relevant, the optical detectors 130a, 130b may operate merely to determine the quantity of light incident on the optical detectors 130a, 130b. In such examples, the optical detectors 130a, 130b may be area detectors such as single pixel detectors, single photon counters, or CCD/CMOS cameras that provide an aggregate signal rather than a pixelated signal. The pixelated detectors may be pixelated with the light from all pixels or a portion of the pixels being integrated to determine a quantity of light incident on the detectors.

It is to be appreciated that aspects of the present invention are valuable even when the object 1 is not resolvable by the optical system, i.e., collection optics 110 and the optical detectors 130a, 130b. In other words, the acoustic signature of the object 1 can still be obtained and characteristics of the object 1 can be determined, even if the optical portion of the apparatus 100 is unable to sufficiently resolve the object 1. For example, a remote satellite or vehicle that would not result in a suitable visual image may still provide polarization data sufficient to resolve the acoustic signature. Furthermore, in some examples, the optical detectors 130a, 130b may operate as a photon counter, outputting a stream of numerical values indicative of the time of arrival of each photon incident on the optical detector. This may be useful in determining the acoustic properties of the object 1.

The first optical detector 130a may generate a first signal, and the second optical detector 130b may generate a second signal. The signals generated by each optical detector 130a, 130b contain information regarding the amount of light of a given polarization that is received from the object 1 at a given point in time. The signals may be generated continuously at the maximum sampling rate allowed by the optical detectors 130a, 130b. The processor 140 may group signal data according to time segments, or periods of duration. This may allow the apparatus 100 to easily synchronize and compare the signals. By calculating a difference between the first signal corresponding to a selected time segment, and the second signal corresponding to the same selected time segment, and observing the change in the differences over time, it is possible to gain insights into the object 1, e.g., to identify the object, determine the state of operation of the object and/or determine functions of the object. Furthermore, in one example, the difference is divided by the sum of the first signal over the selected time segment and the second signal over the same selected time segment to provide a normalization factor. It will be appreciated that, in some examples, normalization may make the data based on the difference more reliable by accounting for variations in the total amount of light reflected from the object.

Although the above example was described using a difference between the first and second signals over a selected time segment, other operators comparing the first and second signals over a selected time segment may be used to gain information regarding the quantity of light in the first pathway and the quantity of light in the second pathway. For example, a ratio of the first and second signals over a selected time segment may be used.

The rate at which the signals are generated (i.e., the rate at which outputs from the first optical detector and the second optical detector are created) may be determined at least in part by the frequency of the vibration of the object 1 to be measured. It will be appreciated that it is desirable that the rate be at least at the Nyquist rate, or the minimum rate at which a signal can be sampled without introducing errors, which is generally twice the highest frequency present in the signal. For example, the rate may be in the range 1 per second to 10,000 per second for frequencies between 0.5 Hz and 5,000 Hz, although any suitable rate may be used that current technology permits or that yet-to-be produced technology may permit. For example, the rate may be 1500 per second. In some embodiments, the rate is set at the photon limit (i.e., based on the ability of the collection optics 110 to collect photons and the ability of the optical apparatus 110 to transmit and detect the photons).

At least one processor 140 is in communication with the first and second optical detectors. In the illustrated embodiment, processor 140 is coupled in communication with the optical detectors 130a, 130b. The processor 140 may be any suitable computer processor for receiving and manipulating signal data from the detectors 130a, 130b. For instance, the processor 140 may be commonly used computer processors such as those having x86, x64, or ARM, PIC, or Arduino architecture. The apparatus 100 may comprise multiple local processors 140 for additional data processing or speed capabilities. The apparatus 100 may comprise a distributed network of processors 140, depending on implementation. Many aspects of the invention may take the form of computer-executable instructions, including algorithms executed by a programmable computer. Those skilled in the relevant art will appreciate that the invention can be practiced with other computer system configurations as well. Certain aspects of the invention can be embodied in a special-purpose computer or data processor that is specifically programmed, configured or constructed to perform one or more of the computer-executable algorithms described below. Accordingly, the term "computer" as generally used herein refers to any data processor and includes Internet appliances, hand-held devices (including palm-top computers, wearable computers, cellular or mobile phones, multi-processor systems, processor-based or programmable consumer electronics, network computers, minicomputers) and the like.

Some aspects of the invention may also be practiced in distributed computing environments, where tasks or modules are performed by remote processing devices that are linked through a communications network. In a distributed computing environment, program modules or subroutines may be located in both local and remote memory storage devices. Aspects of the invention described below may be stored or distributed on computer-readable media, including magnetic and optically readable and removable computer disks, fixed magnetic disks, floppy disk drive, optical disk drive, magneto-optical disk drive, magnetic tape, hard-disk drive (HDD), solid state drive (SSD), compact flash or non-volatile memory, as well as distributed electronically over networks. Data structures and transmissions of data particular to aspects of the invention are also encompassed within the scope of the invention.

The processor 140 may additionally include or be in communication with computer-readable memory 142 and a power supply 144. The memory 142 may be any memory suitable for signal processing, and may include both RAM and permanent storage. The power supply 144 may be any suitable power supply, including alternating or direct current, and may be fed by a wall outlet, generator, battery, photovoltaic cell, or any combination thereof. The processor 140 may include any other necessary components commonly used with computers, including motherboards, housing, input/output panels, display modules, analog-to-digital converters, network connections, and the like.

The processor 140 receives the first and second signals from the first and second optical detectors 130a, 130b, respectively. The processor 140 is then programmed to calculate a difference of the first and second signals, a sum of the first and second signals, and a ratio of the difference to the sum. These calculations may be performed for each data point generated by the detectors 130*a*, 130*b* in one example, or over a selected time segment in another example. Calculating the difference of the signals may give a difference in the quantity of light incident on the first and second detectors 130*a*, 130*b* over that time segment. Calculating the sum of the signals may give a total of the quantity of incident light. Calculating the ratio of the difference to the sum may indicate the degree of linear polarization (DOLP) of the incident light. This is because the apparatus 100 has measured, independently and simultaneously, the orthogonal polarization states as separated by the linear polarizer. In this modality, none of the Stokes parameters are being directly measured. However, the change in the DOLP as a function of time is being shown.

The first and second resultant orthogonal signals created by the optical detectors may be subject to a number of factors, including atmospheric transparency, inherent detector noise, the alignment angle of the polarizer, and the maximum and minimum observed intensities.

The processor may generate a signal corresponding to a sequential output of the ratios. Accordingly, it will be appreciated that the signal is indicative of an acoustic signature of the object. Although in the example described above a signal is generated using a difference, other operators comparing the first and second signals over a selected time segment may be used, and sequential outputs of the results of using said operators may be used to generate signals corresponding to an acoustic signature of the object 1.

The processor 140 may perform signal processing operations in order to prepare detected signals for further analysis. For example, common signal processing operations may include noise reduction, normalization, sharpening, and the like. Additional signal processing operations may include processing according to Mie theory to address atmospheric scattering, and Fourier transformation to modify the domain of the captured signals. Mie scattering may occur as the incident light travels through the atmosphere and interacts with particles with diameters similar to its wavelength. Mie theory may make the scattered signals more accurate and usable. Additional scattering treatments may be applied, according to Rayleigh scattering theory, discrete dipole approximation, and other computational techniques. Fourier transformation may transform the signals into the frequency domain, allowing the processor 140 to analyze the signals based on the frequencies present rather than the intensity of the signals. It will be appreciated that such frequency information may be highly indicative of the nature of the vibrations of object 1, as the frequencies of the vibrations may correspond to acoustic frequencies of or propagating through the object 1 itself. It will especially be appreciated that peaks in the frequency values may correspond to resonance frequencies of the object 1.

Additional techniques for time-series acoustic sampling may be employed instead of, or in combination with, any of the above techniques. For example, the signals may be autocorrelated in order to discover periodic signals, or beats, in the time domain. Time transient signals may rely on different implementations of looking at frequency distributions. For example, a Wigner distribution may be used to find chirp tones.

In one example, the signals are divided into temporal segments and a transform is performed separately on each segment, and the variations in the frequency content of each segment are analyzed to determine changes in the acoustic signature over time. The length and number of each segment may be the same in one example, or may be different from segment to segment. The length and number of each segment may depend on the signal intensity, capture time, object size, number of frequencies present, and other factors. For example, a segment may have a length of about 256 samples or data points, and a measurement may contain about 100 segments. In another example, a segment may have between 30 and 100,000 samples. In another example, a measurement may contain between 1 and 100 segments. More or fewer samples, and more or fewer segments may be included, depending on the construction of the apparatus 100. A bandpass, high pass and/or low pass filter may be used to filter the signal and eliminate or reduce frequencies known to contain excessive noise.

After the first and second signals have been compared, and the processor has calculated a difference, a sum, and a ratio of the difference to the sum, the resultant data may indicate the DOLP over the selected period of time. The data may be normalized for further analysis. The processor 140 may next generate a signal corresponding to a sequential output of the ratios. This signal is indicative of an acoustic signature of the object being sensed. To derive acoustic signatures from this resultant data, the processor 140 may calculate power spectra for the resultant data stream to reveal any acoustic signal present. The power spectrum describes the distribution of power over time into frequency components composing the signal. Peaks in the spectra may represent the frequencies of physical resonant vibrations on or from the object 1. A periodogram may be calculated for the entire duration of the signals and normalized. In one example, the periodograms of each segment may be averaged using overlapping windows. This may improve the accuracy of the power determination while limiting the frequency resolution. Additionally, the power spectra data may be used to calculate a spectrogram of the frequencies detected as a function of time for the measured object 1. The spectrogram may be calculated from the power spectra of successive short sequences of the DOLP time series. In one example, each sequence may overlap. The spectrogram may allow a user to observe changes in the spectral content of the DOLP signal.

The generated signal may be output by the processor 140. In one example, the generated signal may be stored in computer-readable memory 142 on the apparatus 100 or in a connected database. In another example, the generated signal may be output digitally to a display screen, visual file, numerical entry, or text data. In yet another example, the generated signal may be printed or otherwise indicated in hard copy format. The apparatus 100 may output the generated signal in any combination of formats. In another example, the apparatus 100 may compile a number of generated signals and other relevant data into a file, report, or other format.

In one example, where an optical detector comprises an array of pixels, the photons from object 1 or a relevant portion of object 1 may be directed only onto a limited portion of the array. For example, such an occurrence may result where collection optics 110 are configured to receive photons from a set field of view, such as when the collection optics 110 are staring, and the object 1 moves within the field of view. In such examples, it may be advantageous if a determination of the quantity of light in a given time segment of a series is calculated using an output of the optical detector from only the selected segment of the array, particularly the portion of the array receiving photons from the object 1. In such examples, the segment for which the quantity of light is calculated may be movable in a manner to track the object within the field of view. In other words, the object may be electronically tracked within the field of view. In one example, electronic tracking may be used in combination with mechanical tracking using movement of the collection optics 110. It will be appreciated that such tracking may be effective in increasing the signal-to-noise of the signal output from the processor 140.

In one example, light from a passive or natural source is incident on object 1, which results in reflected photons from object 1 that are collected by collection optics 110 to generate the incident light on the apparatus 100. For example, the light may be sun light, moon light, star light or ambient light present indoors. Alternatively, remote sensing apparatus 100 may comprise one or more light sources 150 to produce light in a desired band of electromagnetic radiation that can be operated to direct light onto object 1 to generate photons to be collected by the collection optics 110. In one example, it is advantageous if the light source 150 is (or light sources are) point sources; however, in one example, the light sources may be non-point sources.

In one example, it is advantageous if a signal from processor 140 (generated as described above) is output from the processor to an output sound transducer 160 such that the remotely sensed vibrations are used to generate a corresponding audible output. For example, such an output transducer may be useful where a human ear is particularly sensitive to a particular portion of the sound output or is particularly adept at identifying a relevant sound pattern. In some cases, the frequencies detected may be outside of human hearing range. In one example, the signal may be modulated—for instance, by single side-band modulation—to bring these infrasounds into the audible range by shifting the frequencies to those suitable for human hearing.

The apparatus 100 may be partially or entirely contained in a housing (not shown). The housing may be any container, enclosure, or holding form factor suitable to hold the apparatus 100. The collection optics 110 may be located outside the housing, and may direct photons from object 1 into the housing and the optical system within. The components within the housing may be mounted using any suitable materials and techniques, including optical rails, mounts, tubes, epoxy, adhesive, and the like.

Figure 2:
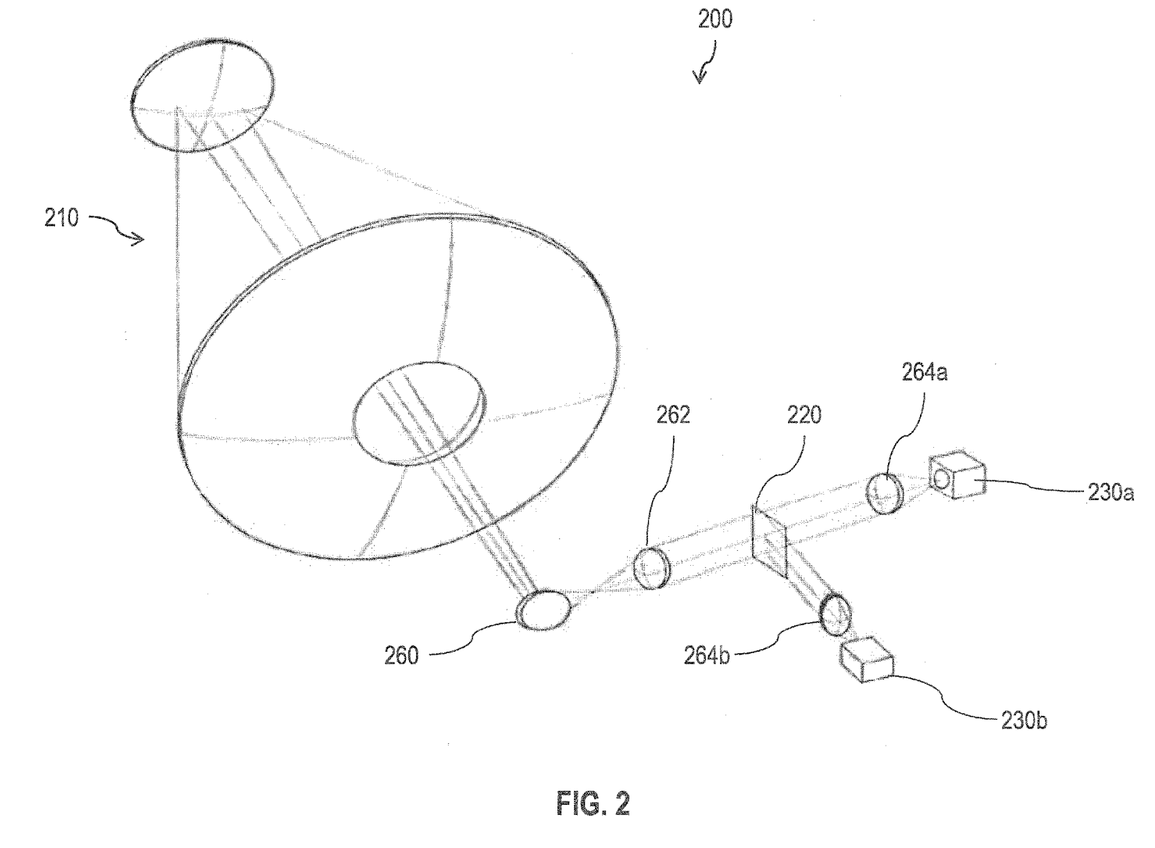
FIG. 2 is a perspective illustration of the remote sensing apparatus of FIG. 1, in accordance with the first exemplary embodiment of the present invention.

FIG. 2 is a perspective illustration of the remote sensing apparatus 200 of FIG. 1. FIG. 2 shows an exemplary implementation of the optical system of the apparatus 200, including collection optics 210, directing optics 260, focusing elements 262, 264a, 264b, beam splitter 220, and optical detectors 230a, 230b. In this example, the collection optics 210 are of a Cassegrain design and operate to direct photons to directing optics 260, which are shown as a mirror. In another example, directing optics 260 may be a prism or other elements suitable for orienting the apparatus 200 in a desired direction. The directing optics 260 direct the photons into a first focusing element 262, which collimates the incident beam of light before it reaches the beam splitter 220. The first focusing element 262 may be any suitable lens or combination of elements suitable to collimate light in the desired band of the electromagnetic spectrum. The beam splitter 220 divides the light into two pathways where the light in each pathway is linearly polarized and the linear polarizations are orthogonal to one another (i.e., the pathways are p and s polarized, respectively). Second and third focusing elements 264a, 264b, respectively, focus the light from each pathway onto the optical detectors 230a, 230b, respectively.

Figure 3:
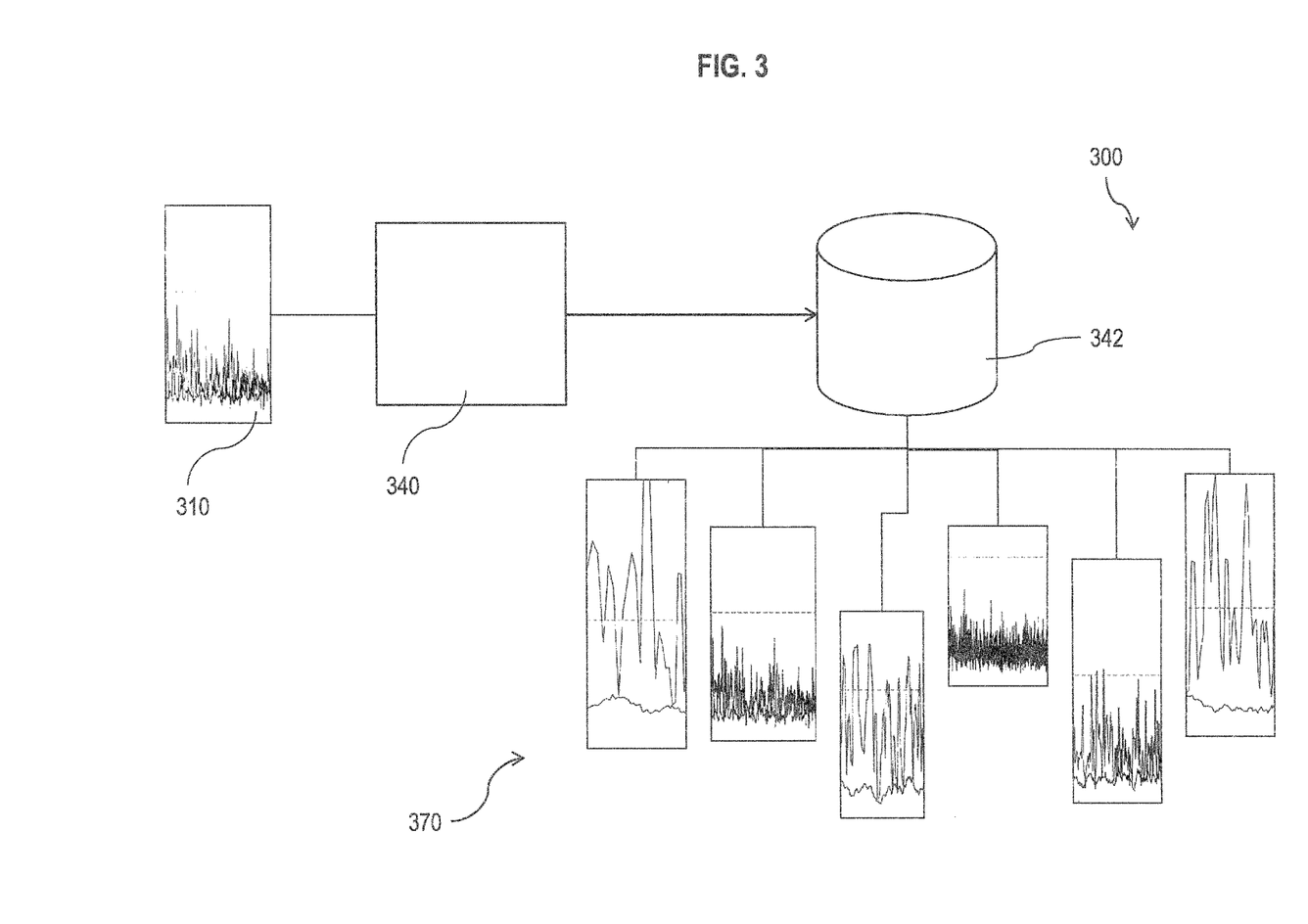
FIG. 3 is a schematic illustration showing a library of acoustic signatures, in accordance with the first exemplary embodiment of the present invention.

FIG. 3 is a schematic illustration showing a library 300 of acoustic signatures. In one example, it may be advantageous to have a library 300 of acoustic signatures with which a signal output 310 from the processor 340 can be compared, e.g., by performing a correlation calculation. The library 300 may include acoustic signatures for known objects, such as satellites, spacecraft, vehicles, and the like. The library 300 may include acoustic signatures for known objects in known environments, such as in space, high altitude, inclement weather, and the like. The library 300 may include a collection of acoustic signatures for known activities, such as the operation of a mechanical piece or extension of solar panels. The activities may be further categorized based on whether they are running normally, i.e., the components are functioning well, or running abnormally, i.e., a component may be failing or functioning improperly. The library 300 may include only partial acoustic signatures as well. In one example, the library 300 may be comprised of entries 370, where each entry is the signal output from processor 140 of the remote sensing apparatus 100 when it is receiving light from a known object in a known state (i.e., it is the acoustic signature of a known object 1 operating in a known manner). The entries may be stored as digital files on computer-readable memory 342 which may be the on-board memory of the apparatus 100 relative to FIG. 1, or a connected database. The database may be connected locally or remotely by a network system. The processor 340 may be programmed to compare the signal output 310 with the library entries 370. The comparison may utilize machine learning, deep learning, neural networks, or other computational techniques to find signal patterns that match. Comparisons of this nature may use the database entries 370 to train the processor 340 which factors are indicative of certain objects, environments, activities, and the like. In one example, one or more machine learning techniques, such as principal component analysis, may be used. In another example, the entries 370 may be converted into audio fingerprints, where the data-heavy digital frequency information is converted into easy-to-search numeric and hash values. These numeric and hash values may be normalized and compared against the signal output 310 to detect matching values or patterns of values. In one example, t-distributed stochastic neighbor embedding (t-SNE) may be used. It will be appreciated that information regarding an unknown object could be determined when there is a correlation between the acoustic signature in the library 300 and a signal from the processor 140 when it is observing the unknown object. The processor 140 may compare the library entries 370 directly, or it may convert the unknown data into audio fingerprints for faster searching. The comparison may be performed contemporaneously with the signal acquisition, i.e., as the apparatus 100 is collecting the photons. In another example, the comparison may be performed after the entire signal 310 has been captured and processed.

Figure 4:
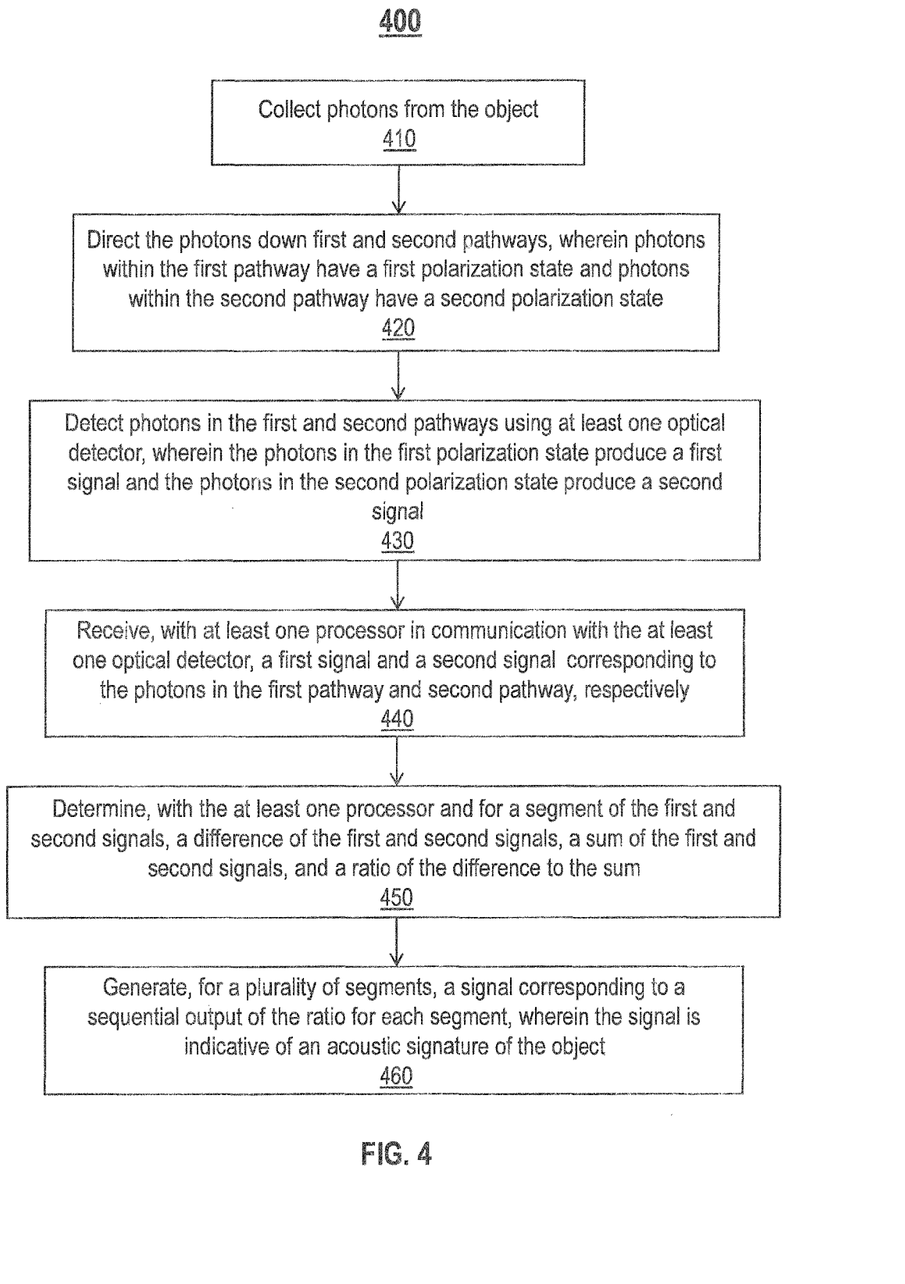
FIG. 4 is a flowchart illustrating a photo-acoustic, polarimetric method of remotely sensing an object, in accordance with the first exemplary embodiment of the present invention.

FIG. 4 is a flowchart 400 illustrating a photo-acoustic, polarimetric method of remotely sensing an object, in accordance with the first exemplary embodiment of the present invention. It should be noted that any process descriptions or blocks in flow charts should be understood as representing modules, segments, portions of code, or steps that include one or more instructions for implementing specific logical functions in the process, and alternate implementations are included within the scope of the present disclosure in which functions may be executed out of order from that shown or discussed, including substantially concurrently or in reverse order, depending on the functionality involved, as would be understood by those reasonably skilled in the art of the present disclosure.

Step 410 includes collecting photons from the object. The collection optics 110 may be those discussed relative to FIG. 1, such as reflective or refractive telescopes, zoom lenses, or other optics.

Step 420 includes directing the photons down first and second pathways, wherein photons within the first pathway have a first polarization state and photons within the second pathway have a second polarization state. The input beam may be split by one or more polarizing beam splitters, beam splitting plates, birefringent glass, prisms, and the like. The angular deviation between the first and second pathways may be any suitable deviation necessary to separately detect the first and second pathways. For instance, when certain prisms are used, as will be discussed further in FIG. 5, below, the angular deviation may be small, up to several degrees. When a polarizing beam splitting cube is used, the angular deviation may be much greater, up to about 90° or more. The proper angular deviation may depend on the optical system design.

Step 430 includes detecting photons in the first and second pathways using at least one optical detector, wherein the photons in the first polarization state produce a first signal and the photons in the second polarization state produce a second signal. In one example, a single optical detector may be used to detect both the first and second pathways. The photons in the pathways, may strike different portions of the optical detector, allowing the detected signals to be calculated independently. In another example, multiple detectors may be used. For instance, one detector may be placed in each pathway to detect the incident light separately. In one example, more than two detectors may be used to create spatial separation in the detected data.

Step 440 includes receiving, with at least one processor in communication with the at least one optical detector, a first signal and a second signal corresponding to the photons in the first and second pathways, respectively.

Step 450 includes determining, with the at least one processor and for a segment of the first and second signals, a difference of the first and second signals, a sum of the first and second signals, and a ratio of the difference to the sum. Where the first and second signals both come from a single optical detector, the signals may need to be separated by the processor before the determinations can be made. Separation may simply include recording values in different areas or different pixels on the optical detector separately. In one example, separation may require noise reduction operations to ensure that the signal data is truly separate, especially at the part of the optical detector where the two pathways hit nearest each other. Additional signal processing, as discussed relative to FIG. 1, above, may be performed by the processor.

Step 460 includes generating a signal for a plurality of segments corresponding to a sequential output of the ratio for each segment, wherein the signal is indicative of an acoustic signature of the object. The generated signal may be the signal discussed relative to FIG. 1, above, and may be useful as an acoustic indicator of the nature, operation, or state of the object being sensed.

The method may further include any other features, components, or functions disclosed relative to any other figure of this disclosure.

Figure 5:
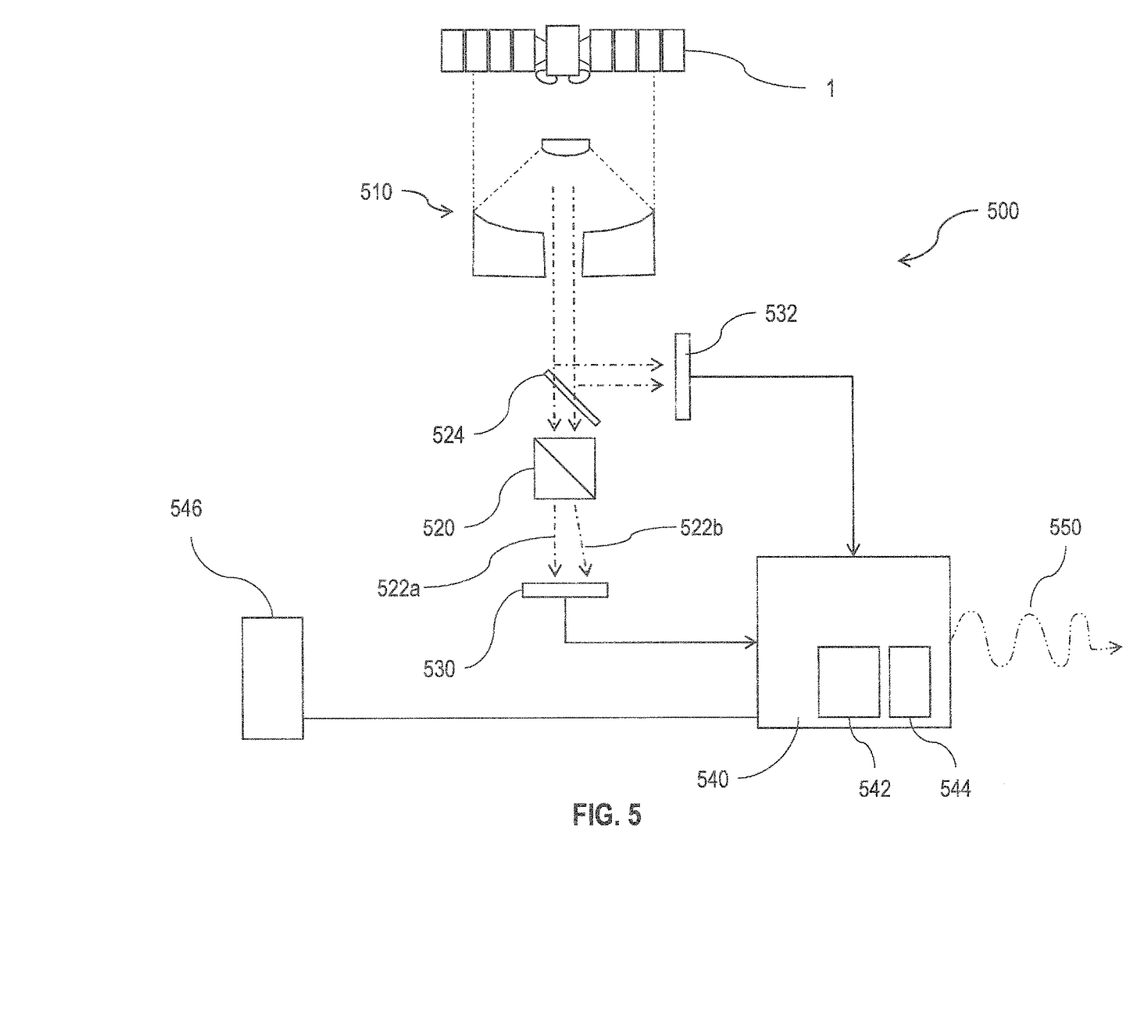
FIG. 5 is a schematic block diagram of a remote sensing apparatus, in accordance with a second exemplary embodiment of the present invention.

FIG. 5 is a schematic block diagram of a remote sensing apparatus 500 in accordance with a second exemplary aspect of the present invention. The apparatus 500 includes collection optics 510 directing photons from an object 1. A polarizing prism 520 angularly separates the photons into a first polarization state 522a and a second polarization state 522b. An optical detector 530 is included. A first portion of the optical detector 530 receives the photons in the first polarization state 522a, and a second portion of the optical detector 530 receives the photons in the second polarization state 522b. At least one processor 540 is in communication with the optical detector 530. The at least one processor 540: receives a signal from the optical detector 530, wherein a first portion of the signal corresponds to the photons in the first polarization state 522a, and a second portion of the signal corresponds to the photons in the second polarization state 522b; calculates, for a segment of the first and second signals, a difference of the first and second portions of the signals, a sum of the first and second portions of the signals, and a ratio of the difference to the sum; and generates, for a plurality of segments, a signal 550 corresponding to a sequential output of the ratio for each segment. The signal is indicative of an acoustic signature of an object 1 being sensed.

Many aspects of the optical system of apparatus 500 may be the same or similar to those discussed relative to FIGS. 1 and 2, above. For instance, the collection optics 510, the optical detector 530, and the other optical elements such as directing optics and focusing optics (not shown) may be used. The collection optics may direct photons from object 1 into the rest of the apparatus 500.

The photons may be directed to a polarizing prism 520. The polarizing prism 520 may angularly separate the incident photon beam into two beams having two different polarization states. The polarizing prism 520 may be any suitable birefringent polarizers, such as Glan-Taylor polarizers, Glan-Thompson polarizers, Wollaston prisms, Rochon prisms, and the like. By way of example, Wollaston prisms may provide a symmetric deviation between the first and second beams while maintaining substantially equal intensities across both beams. In one example, multiple prisms 520 may be used to separate the beams, separate the polarization states, equalize the beam intensities, or direct the beam path.

The photon beam may be separated into photons in a first polarization state 522a and a second polarization state 522b. The photons from the first polarization state 522a may be linearly polarized and orthogonal to the photons from the second polarization state 522b. In one example, the photons may be circularly or elliptically polarized by introduction of a quarter wave plate. The photons from both states 522a, 522b may hit the optical detector 530 along different portions of the detector surface. A first portion of the optical detector 530 may receive the photons from the first state 522a, and a second portion of the optical detector 530 may receive the photons from the second state 522b. In one example, the signals created by the first and second polarization states 522a, 522b may be individually resolvable due to the angular separation of the photons in the first and second polarization states 522a, 522b. In another example signal processing may be required to separate a portion of the signals.

The at least one processor 540 may be any of the processors and accompanying components 542, 544 as discussed relative to FIG. 1, above. The processor 540 may receive a signal from the optical detector 530, wherein a first portion of the signal corresponds to the photons in the first polarization state 522a, and a second portion of the signal corresponds to the photons in the second polarization state 522b. The first and second portions of the signal may correspond with the number or intensity of photons incident upon the optical detector 530 relative to the first and second polarization states 522a, 522b. The processor 540 may calculate a difference of the first and second portions of the signals, a sum of the first and second portions of the signals, and a ratio of the difference to the sum. This operation may be similar to the calculation performed relative to FIG. 1, above. The processor 540 may generate a signal 560 corresponding to a sequential output of the ratios. The signal 560 may directly express the degree of polarization of the input photons, and may vary in magnitude over time. As discussed above, the variations in magnitude over time may be transformed or otherwise used to determine oscillating frequencies coming from the object 1. These frequencies can be used to create an acoustic signature of the object 1. The signal 560 may be further processed to make it easier to hear, to filter noise, or to focus on particular frequencies present. The signal 560 may be fed to an acoustic transducer, output to a screen, report, or other file, or compared against a library of entries as discussed in FIG. 3.

In one example, the apparatus 500 may include a flip mirror 524 that can be moved into and out of the beam path before the photons reach the polarizing prism 520. The flip mirror 524 may be used to direct the incoming photons to an acquisition detector 532. The acquisition detector 532 may be an optical detector as discussed relative to FIG. 1, including a CCD or CMOS camera. It may be in communication with the processor 540. The acquisition detector 532 may be used to locate or focus in on the object 1. This may be especially helpful when the desired imaging band is in the visible spectrum. The image provided by the acquisition detector may allow a user to align the apparatus 500 or to track the object 1. In one example, the image data may not be considered by the processor 540 in the acoustic signature calculations below. In another example, the image data may be used as a visual overlay to show, spatially, where measured frequencies originated from on the object 1. The acquisition detector may additionally be used with the other aspects of this disclosure.

In another example, the apparatus 500 may further include an accelerometer 546. The accelerometer 546 may provide 3-axis motion and directional data relative to the position and movement of the apparatus 500. The accelerometer 546 may be in communication with the processor 540, which may provide the data to a user. In one example, movement of the apparatus 500 may be controlled by a computerized motor, such as a stepper motor, capable of tracking GEO objects as they travel across the sky. The data from the accelerometer 546 may allow the motor to maintain an accurate tracking position.

Figure 6:
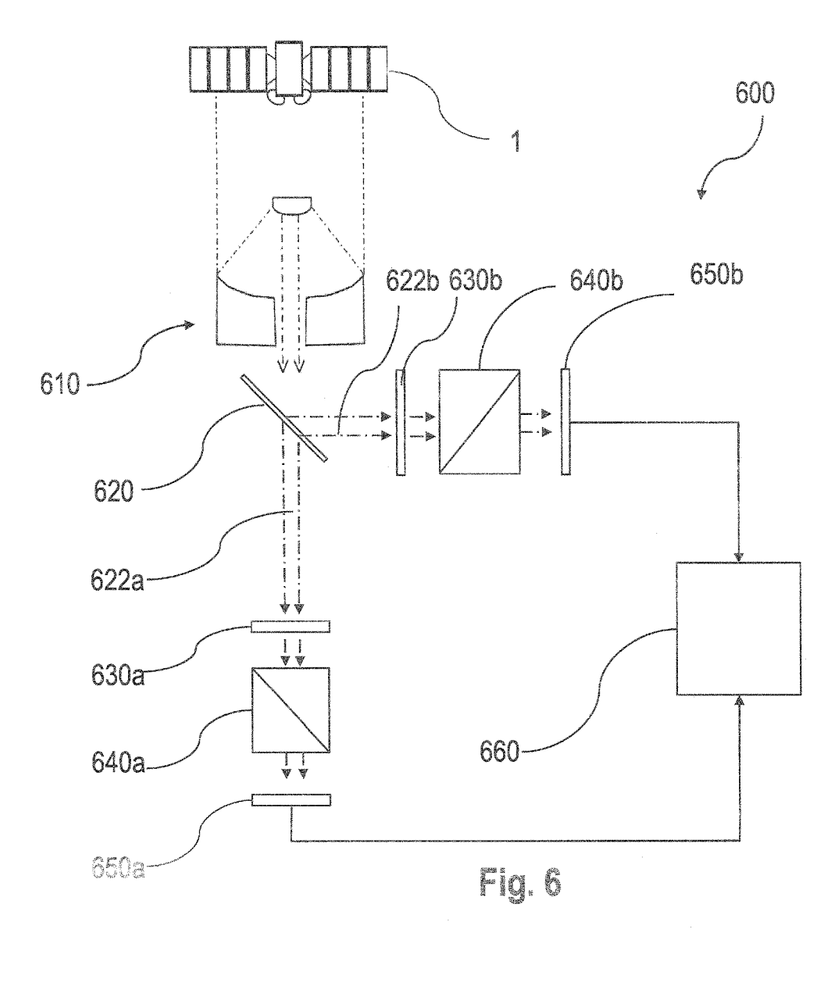
FIG. 6 is a schematic block diagram of a remote sensing apparatus, in accordance with a third exemplary embodiment of the present invention.

FIG. 6 is a schematic block diagram of a remote sensing apparatus 600, in accordance with a third exemplary embodiment of the present invention. The apparatus 600 may remotely detect the modulation of circularly polarized light incident upon the apparatus 600. The apparatus 600 may include collection optics 610 to collect and receive photons from an object 1. The collection optics 610 may direct light from the object 1 down an optical path. In one example, the light is split by a 50/50 beam splitter 620 that divides the light into two pathways 622a, 622b of approximately equal intensity. The light may not be polarized at this time. The light in each pathway 622a, 622b may further be directed through respective quarter waveplates 630a, 630b and then through respective linear polarizers 640a, 640b. The quarter waveplates 630a, 630b and linear polarizers 640a, 640b may be selected to separate the light in the pathways 622a, 622b into left and right circularly polarized light. For example, light in the first pathway 622a may be left circularly polarized, while light in the second pathway 622b may be right circularly polarized. The 50/50 beamsplitter 620 may be any suitable plate, circular filter, tube, cube, or the like for dividing light into two distinct pathways. The quarter waveplates 630a, 630b and linear polarizers 640a, 640b may be any suitable quarter waveplates and linear polarizers commonly used, depending on the spectrum of light being detected.

Circularly polarized light from pathways 622a, 622b may hit photodetectors 650a, 650b, respectively, located in the pathways. The photodetectors 650a, 650b may be in communication with a processor 6560 as described above relative to FIGS. 1 and 5. The photodetectors 650a, 650b may communicate first and second signals to the processor 660 as light is detected. The processor 660 may calculate a difference of the first and second signals, a sum of the first and second signals, and a ratio of the difference to the sum. This operation may be similar to the calculation performed relative to FIG. 1, above. The processor 660 may generate a signal corresponding to a sequential output of the ratios. The signal may directly express the degree of polarization of the input photons, and may vary in magnitude over time. As discussed above, the variations in magnitude over time may be transformed or otherwise used to determine oscillating frequencies coming from the object 1. These frequencies can be used to create an acoustic signature of the object 1. The signal may be further processed to make it easier to hear, to filter noise, or to focus on particular frequencies present. The signal may be fed to an acoustic transducer, output to a screen, report, or other file, or compared against a library of entries as discussed in FIG. 3.

It should be emphasized that the above-described embodiments of the present disclosure, particularly, any "preferred" embodiments, are merely possible examples of implementations, merely set forth for a clear understanding of the principles of the disclosure. Many variations and modifications may be made to the above-described embodiment(s) of the disclosure without departing substantially from the spirit and principles of the disclosure. Particularly, any aspect of this disclosure may be used by, combined with, or added onto any other aspect of this disclosure. All such modifications and variations are intended to be included herein within the scope of this disclosure and the present disclosure and protected by the following claims.

What is claimed is:

1. A photo-acoustic polarimetric remote sensing apparatus, comprising:
   a telescope directing visible light photons from an object;
   a polarizing beam splitter in optical alignment with the telescope, the polarizing beam splitter having first and second pathways corresponding to first and second polarization states, respectively, wherein the first and second pathways are substantially perpendicular;
   a first photodetector in optical alignment with the first pathway;
   a second photodetector in optical alignment with the second pathway;
   at least one processor in communication with the first and second photodetectors, wherein the at least one processor generates a signal corresponding to a degree of linear polarization of the photons over time, wherein the signal is indicative of an acoustic signature of the object.

2. A photo-acoustic polarimetric remote sensing apparatus, comprising:
   collection optics directing photons;

a polarizing beam splitter having first and second pathways, wherein photons within the first and second pathways have first and second polarization states, respectively;

a first optical detector located in the first pathway;

a second optical detector located in the second pathway; and at least one processor in communication with the first and second optical detectors, wherein the at least one processor:

receives first and second signals from the first and second optical detectors, respectively;

calculates, for a segment of the first and second signals, a difference of the first and second signals, a sum of the first and second signals, and a ratio of the difference to the sum; and generates, for a plurality of segments, a signal corresponding to a sequential output of the ratio for each segment, wherein the signal is indicative of an acoustic signature of an object being sensed.

3. The apparatus of claim 2, wherein the collection optics are one of: a Cassegrain, a Gregorian, a modified Dahl-Kirkham, a Keplerian, and a Ritchey-Chretien telescope.

4. The apparatus of claim 2, further comprising a light source to illuminate the object being sensed.

5. The apparatus of claim 2, further comprising a sound transducer in communication with the at least one processor, wherein the at least one processor communicates the signal indicative of an acoustic signature of the object to the sound transducer, and wherein the sound transducer generates an audible output.

6. The apparatus of claim 2, wherein the first and second detectors transmit the first and second signals at a rate of at least 10 Hz.

7. The apparatus of claim 2, wherein the generated signal comprises a power spectra measurement for the ratios over a series of time segments.

8. The apparatus of claim 2, wherein the generated signal comprises a spectrogram of detected acoustic frequencies over time.

9. A photo-acoustic, polarimetric method of remotely sensing an object, comprising the steps of:

collecting photons from the object;

directing the photons down first and second pathways, wherein photons within the first pathway have a first polarization state and photons within the second pathway have a second polarization state;

detecting photons in the first and second pathways using at least one optical detector, wherein the photons in the first polarization state produce a first signal and the photons in the second polarization state produce a second signal;

receiving, with at least one processor in communication with the at least one optical detector, a first signal and a second signal corresponding to the photons in the first pathway and second pathway, respectively;

determining, with the at least one processor and for a segment of the first and second signals, a difference of the first and second signals, a sum of the first and second signals, and a ratio of the difference to the sum; and generating, for a plurality of segments, a signal corresponding to a sequential output of the ratio for each segment, wherein the signal is indicative of an acoustic signature of the object.

10. The method of claim 9, wherein the step of collecting photons from the object is performed using one of: a Cassegrain, a Gregorian, a modified Dahl-Kirkham, a Keplerian, and a Ritchey-Chretien telescope.

11. The method of claim 9, further comprising the step of providing a light source to illuminate the object being sensed.

12. The method of claim 9, further comprising the step of sending the signal indicative of an acoustic signature of the object to a sound transducer in communication with the at least one processor, wherein the sound transducer generates an audible output.

13. The method of claim 9, wherein the photons are directed down the first and second pathways by a polarizing beam splitter.

14. The method of claim 9, wherein the photons are directed down the first and second pathways by a polarizing prism.

15. The method of claim 9, wherein generating a signal corresponding to the sequential output of the ratio comprises determining a power spectra measurement for the ratios over a series of time segments and determining a spectrogram of detected acoustic frequencies over time.

16. A photo-acoustic polarimetric remote sensing apparatus, comprising:

collection optics directing photons;

a polarizing prism angularly separating the photons into a first polarization state and a second polarization state;

an optical detector, wherein a first portion of the optical detector receives the photons in the first polarization state, and wherein a second portion of the optical detector receives the photons in the second polarization state; and at least one processor in communication with the optical detector, wherein the at least one processor:

receives a signal from the optical detector, wherein a first portion of the signal corresponds to the photons in the first polarization state, and a second portion of the signal corresponds to the photons in the second polarization state;

calculates, for a segment of the first and second signals, a difference of the first and second portions of the signals, a sum of the first and second portions of the signals, and a ratio of the difference to the sum; and generates, for a plurality of segments, a signal corresponding to a sequential output of the ratio for each segment, wherein the signal is indicative of an acoustic signature of an object being sensed.

17. The apparatus of claim 16, wherein the collection optics are one of: a Cassegrain, a Gregorian, a modified Dahl-Kirkham, a Keplerian, and a Ritchey-Chretien telescope.

18. The apparatus of claim 16, wherein the polarizing prism is a Wollaston prism.

19. The apparatus of claim 16, further comprising a flip mirror and an acquisition detector in communication with the at least one processor, the flip mirror located to direct the photons to the acquisition detector.

20. The apparatus of claim 16, wherein the generated signal comprises a power spectra measurement for the ratios over a series of time segments.

* * * * *